United States Patent
Tabery et al.

(10) Patent No.: US 8,201,993 B2
(45) Date of Patent: Jun. 19, 2012

(54) METHOD FOR OPERATING A GAS SENSOR

(75) Inventors: Eric Tabery, Jockgrim (DE); Raphaelle Laure Satet, Stuttgart (DE); Ulrich Eisele, Stuttgart (DE); Lothar Diehl, Gerlingen (DE); Sascha Klett, Oppenweiler (DE)

(73) Assignee: Robert Bosch GmbH, Stuttgart (DE)

( * ) Notice: Subject to any disclaimer, the term of this patent is extended or adjusted under 35 U.S.C. 154(b) by 747 days.

(21) Appl. No.: 12/293,238

(22) PCT Filed: Feb. 12, 2007

(86) PCT No.: PCT/EP2007/051321
§ 371 (c)(1),
(2), (4) Date: Nov. 18, 2008

(87) PCT Pub. No.: WO2007/104622
PCT Pub. Date: Sep. 20, 2007

(65) Prior Publication Data
US 2009/0116534 A1    May 7, 2009

(30) Foreign Application Priority Data
Mar. 16, 2006 (DE) .......... 10 2006 012 476

(51) Int. Cl.
*G01N 25/00* (2006.01)
(52) U.S. Cl. ................ 374/45; 374/50; 374/57
(58) Field of Classification Search ............ 374/45, 374/43, 50, 4, 5, 57
See application file for complete search history.

(56) References Cited

U.S. PATENT DOCUMENTS

| | | | | |
|---|---|---|---|---|
| 4,333,067 A * | 6/1982 | Kugimiya et al. | ............. | 338/34 |
| 4,419,190 A * | 12/1983 | Dietz et al. | ............. | 205/785 |
| 5,177,696 A * | 1/1993 | Bonne | ............. | 702/136 |
| 5,203,278 A * | 4/1993 | Kinney | ............. | 374/E3.001 |
| 5,588,417 A * | 12/1996 | Kotwicki et al. | ............. | 123/697 |
| 5,696,348 A * | 12/1997 | Kawamura et al. | ............. | 374/140 |
| 6,830,372 B2 * | 12/2004 | Liu et al. | ............. | 374/57 |
| 7,036,982 B2 * | 5/2006 | Smith et al. | ............. | 374/144 |
| 7,305,299 B2 * | 12/2007 | Yasui et al. | ............. | 701/109 |
| 7,727,613 B2 * | 6/2010 | Suwabe et al. | ............. | 428/116 |
| 7,875,244 B2 * | 1/2011 | Schlichte et al. | ............. | 422/83 |
| 2003/0006876 A1 * | 1/2003 | Geier et al. | ............. | 338/25 |
| 2003/0012254 A1 * | 1/2003 | Park et al. | ............. | 374/45 |
| 2004/0026408 A1 | 2/2004 | Mormaga et al. | | |
| 2004/0086023 A1 * | 5/2004 | Smith et al. | ............. | 374/141 |
| 2005/0252497 A1 * | 11/2005 | Yasui et al. | ............. | 123/697 |
| 2007/0127544 A1 * | 6/2007 | Huang | ............. | 374/57 |

(Continued)

FOREIGN PATENT DOCUMENTS
DE    40 33 667    5/1991
(Continued)

OTHER PUBLICATIONS

Biance A-L et al: "Leidenfrost drops" Physics of Fluids AIP USA, Bd. 15, Nr. 6, Jun. 2003, pp. 1632-1637.

*Primary Examiner* — Yaritza Guadalupe-McCall
(74) *Attorney, Agent, or Firm* — Merchant & Gould P.C

(57) ABSTRACT

The invention relates to a method for operating a sensor, in particular a sensor made of ceramic material. Said sensor is heated to a shock-resistance temperature which is higher than a specific temperature.

10 Claims, 3 Drawing Sheets

U.S. PATENT DOCUMENTS

| | | | |
|---|---|---|---|
| 2007/0176516 A1* | 8/2007 | Nagaya et al. | 310/346 |
| 2009/0016934 A1* | 1/2009 | Schlichte et al. | 422/94 |
| 2009/0061738 A1* | 3/2009 | Saka et al. | 451/38 |
| 2011/0036069 A1* | 2/2011 | Hahn | 60/273 |

FOREIGN PATENT DOCUMENTS

| | | |
|---|---|---|
| DE | 199 34 319 | 2/2001 |
| DE | 199 44 555 | 3/2001 |
| DE | 102 33 418 | 2/2003 |
| DE | 695 28 227 | 5/2003 |
| DE | 103 14 754 | 3/2004 |
| DE | 10 2004 035 230 | 3/2005 |
| EP | 0 880 025 | 11/1998 |
| JP | 11264811 | 9/1999 |
| JP | 2000234548 | 8/2000 |
| JP | 2001007469 | 1/2001 |
| JP | 03138560 | 5/2003 |
| WO | WO 2007104622 A1 * | 9/2007 |

* cited by examiner

METHOD FOR OPERATING A GAS SENSOR

TECHNICAL FIELD

Sensors, respectively probes, to determine physical characteristics are diversely employed. For example, provision can be made for temperature, soot and gas sensors in an exhaust gas system of an internal combustion engine, which in connection with a catalytic converter and a closed-loop control make an efficient control of the exhaust gas emissions possible.

BACKGROUND

A stoichiometric air-fuel ratio with lambda equal to 1 in the exhaust gas is adjusted particularly with the aid of lambda sensors. In so doing, the lambda value indicates how far the actually prevailing air-fuel mixture deviates from the mass ratio of 14.7 kg air to 1 kg fuel, which is theoretically necessary for complete combustion. Lambda is in this case the quotient from the air mass, which is supplied, and the theoretical air requirement.

The mode of operation of the lambda probe is based on the principle of a galvanic oxygen concentration cell with a solid state electrolyte. The solid state electrolyte typically consists of two interfaces separated by a ceramic. The ceramic material used becomes conductive for oxygen ions at approximately 350° C., so that the so-called Nernst voltage is then produced when the percentage of oxygen is different on both sides of the ceramic, which is situated between the interfaces. This electrical voltage is a measurement of the ratio of the oxygen partial pressures on both sides of the ceramic. Because the residual oxygen content in the exhaust gas of an internal combustion engine is dependent to a great degree on the air-fuel ratio of the mixture supplied to the engine, it is possible to use the oxygen percentage in the exhaust gas as a measurement for the actually prevailing air-fuel ratio.

The operational temperature of the sensors is as a rule specified by the manufacturer and typically lies between 750° and 800° C.

Also in the case of other sensors, it is often necessary to heat the sensor up to an operational temperature when starting the engine. In order to receive utilizable measurement signals as early on as possible—preferably still during the warm-up phase of the internal combustion engine—it is desirable to heat up the sensor as quickly as possible.

When starting the internal combustion engine and particularly in this case a cold internal combustion engine, water vapor developing during combustion can condense on the cold surface areas of the exhaust gas tract in the form of water drops.

If a water drop hits the ceramic surface area of a sensor, the regional cooling down induced by the water drop can be so great that the ceramic is destroyed on account of the temperature differences and the thermal tensions connected with them.

A gas probe is known, for example, from the German patent DE 199 34 319 A1, which has a protective pipe to protect the ceramic sensor element. An additional inner pipe with openings for the admission and emission of the measurement gas, respectively the exhaust gas, is supposed to protect the ceramic sensor element from direct contact with the water.

A method for operating a gas probe is known from the patent 10 2004 035 230 A1, wherein operating states of the internal combustion engine are ascertained. When an operating state prevails, wherein a lower temperature is to be expected in the exhaust gas tract, i.e., for example, during a cold start-up, the sensor is adjusted to a lower temperature or completely switched off. This is done to counter the danger of a thermal shock caused by water. Consequently the sensor has no readiness for closed-loop control during start-up of the internal combustion engine.

SUMMARY

The method according to the invention with the characteristics of the independent claim has in contrast the advantage; in that when a sensor is heated up, i.e. also especially when a cold sensor is heated up in a cold exhaust gas tract, the sensor neither remains switched off nor is operated with a low temperature but is heated to a temperature—a shock resistance temperature—which is higher than a specific operational temperature.

Furthermore a device for the implementation of the method according to the invention is likewise proposed with a temperature default medium, which influences a heating of the sensor in such a way that the sensor has a shock resistance temperature ($T_3$), which is higher than a specific operational temperature.

By means of the steps specified in the independent claims, advantageous modifications and improvements of the method indicated in the independent claim are possible.

It is particularly advantageous for the shock resistance temperature ($T_3$) to be established as a function of a breakdown probability of the sensor. Thus, it is possible in an advantageous manner to adapt the shock resistance temperature to the prevailing type of sensor or to the type of application at hand and to heat up the sensor only to the temperature, from which a sufficient thermal shock safety is present. The shock resistance temperature is preferably selected in such a way that the breakdown probability is less at this temperature than at the specific operational temperature.

Provision is made according to an additional improvement for a measuring operation of the sensor to already occur at the shock resistance temperature. Thus, it is possible that sensor signals can already be evaluated in a phase, wherein in known methods the sensor remains switched off for safety reasons.

Provision is made in an additional embodiment for a measuring operation to occur at a second temperature ($T_2$) after the sensor has been heated up to the shock resistance temperature ($T_3$). This second temperature is preferably the operational temperature of the sensor; and thus, the sensor does not need to be permanently operated at a shock resistance temperature but can advantageously be switched over to a normal operation if the danger of a thermal shock no longer exists.

Provision is made in an additional modification for the sensor to be initially heated to a first temperature ($T_1$) prior to being heated up to the shock resistance temperature ($T_3$). Said temperature ($T_1$) is lower than the second temperature ($T_2$), respectively the specific operational temperature of the sensor. By way of this procedure, the sensor can initially be heated up at lower temperatures and thus be safe from a possibly existing condensate film. The danger is hereby reduced in an advantageous manner; that, for example, due to varied wetting of the sensor when the ceramic is abruptly heated up, thermal tensions are applied, which possibly lead to the destruction of the ceramic.

Provision is made in an additional embodiment for the sensor to be heated up to the shock resistance temperature prior to starting the internal combustion engine. This procedure has the advantage, in that during the start-up of the internal combustion engine and at the first occurrence of a first gas flow in the exhaust gas tract, the sensor is already in operational readiness and can deliver relevant measuring results from the very beginning.

In a further advantageous modification, the shock resistance temperature is maintained at least as long as a dew point end ($t_{TpE}$) is achieved, so that it can be assumed that no condensed fluids are located in the exhaust gas tract and that the sensor can also be safely operated at other temperatures and especially at the operational temperature.

BRIEF DESCRIPTION OF THE DRAWINGS

Examples of embodiment of the invention are depicted in the drawings and are explained in detail in the following description.

The following are shown.

DETAILED DESCRIPTION

The invention is exemplary depicted using a broad band lambda probe. The invention is, of course, also applicable to other lambda probes and also especially to all probes, sensors, sensing devices or like devices, which in their operational readiness are negatively impacted by a thermal shock caused by fluid contact. The danger of a thermal shock particularly arises in regard to sensor materials consisting of ceramic or ceramic like materials, whose structure is easily destroyed by mechanical tensions brought into play. Especially due to the varied linear expansion of the material at varied temperatures, a regional temperature change can cause such great mechanical tensions in the material that the material's durability is exceeded and it breaks. Observations made with a high speed camera show that this initiation of checking occurs only a few ms after contact by the drop of fluid.

Figure 1:
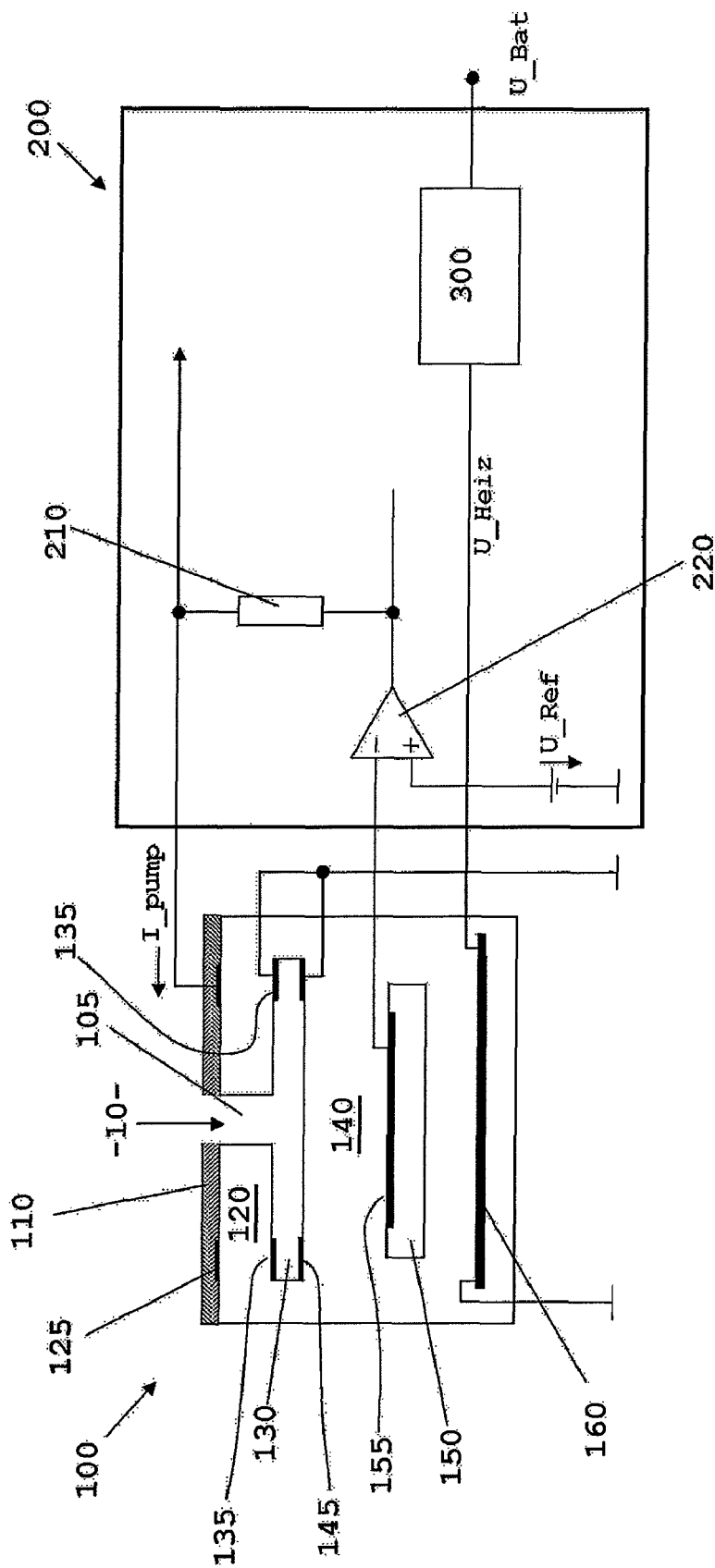
FIG. 1 is a schematic layout of a gas sensor.

FIG. 1 exemplary shows a sensor, respectively a gas sensor 100, for determining the concentration of gas components in a gas mixture with an associated device for its activation 200. The gas sensor is embodied as a broad band lambda probe in the example at hand. Said probe essentially comprises a heater 160 in a lower region, a Nernst cell 140 in a middle region and a pump cell 120 in an upper region. The pump cell 120 has an opening 105 in a central region. Exhaust gas 10 travels through said opening 105 into a measuring chamber 130 of the pump cell 120. Electrodes 135, 145 are disposed at the outer ends of the measuring chamber 130. In this configuration, the upper electrodes 135 are assigned to the pump cell and form the inner pump electrodes (IPE) 135; and the lower electrodes 145 are assigned to the Nernst cell 140 and form the Nernst electrodes (NE) 145. The side of the pump cell 120 facing the exhaust gas has a protective layer 110, inside of which an outer pump electrode (APE) 125 is disposed. A solid state electrolyte, across which oxygen can be transported into the measuring chamber 130 or transported out of the measuring chamber 130 when a pump voltage is present at the electrodes 125, 135, extends between the outer pump electrode 125 and the inner pump electrode 135 of the measuring chamber 130.

An additional solid connects to the pump cell 120. Said solid with a reference gas chamber 150 forms the Nernst cell 140. The reference gas chamber 150 is equipped with a reference electrode (RE) 155 in the direction of the pump cell. The voltage, which arises between the reference electrode 155 and the Nernst electrode 145 in the measuring chamber 130 of the pump cell 120, corresponds to the Nernst voltage. The heater 160 is disposed in a lower region of the further progression of the ceramic.

An oxygen reference gas is held up front in the reference gas chamber 150 of the Nernst cell 140. Via a pump current flowing across the pump electrodes 125 and 135, an oxygen concentration is set in the measuring chamber, which corresponds to a "lambda=1" concentration in the measuring chamber 130.

An activation unit, respectively a control unit 200 conducts the open-loop control of these currents and the evaluation of the Nernst voltage. An operational amplifier 220 measures in this case a Nernst voltage lying at the reference electrode 155 and compares this voltage with a reference voltage U_Ref, which typically lies at approximately 450 mV. When deviations occur, the operational amplifier 220 impresses a pump current to the pump cell 120 via a resistor 210 and to the pump electrode 125, 135.

Additionally a temperature default medium 300 is disposed inside of the control unit 200 in the electrical feed line to the heater 160. Said medium 300 specifies the electrical voltage lying at the heater—and in so doing also indirectly the temperature of the sensor—in a manner suited to the operation of the lambda probe.

Figure 2:
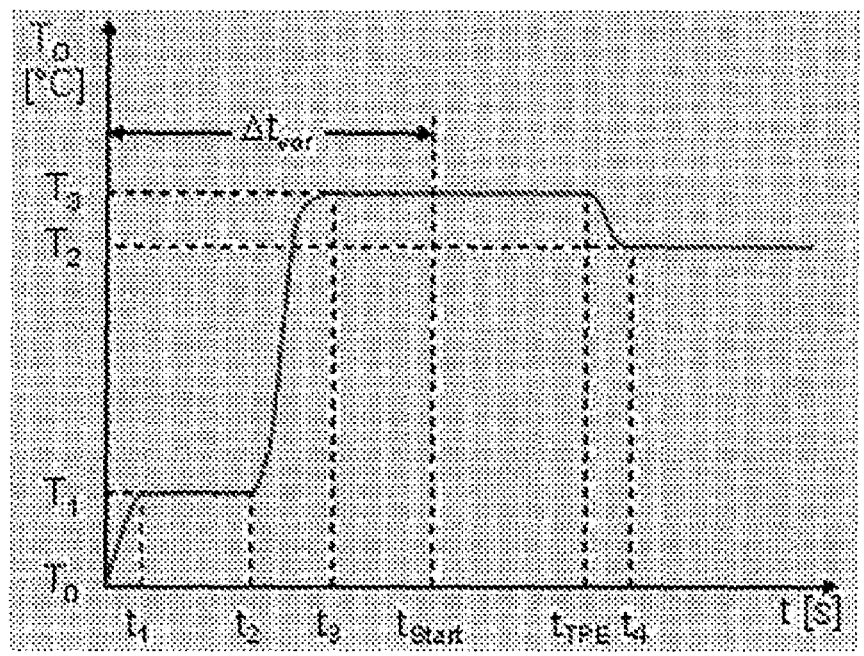
FIG. 2 is a schematic curve of the surface area temperature during a procedure according to the invention.
Figure 3:
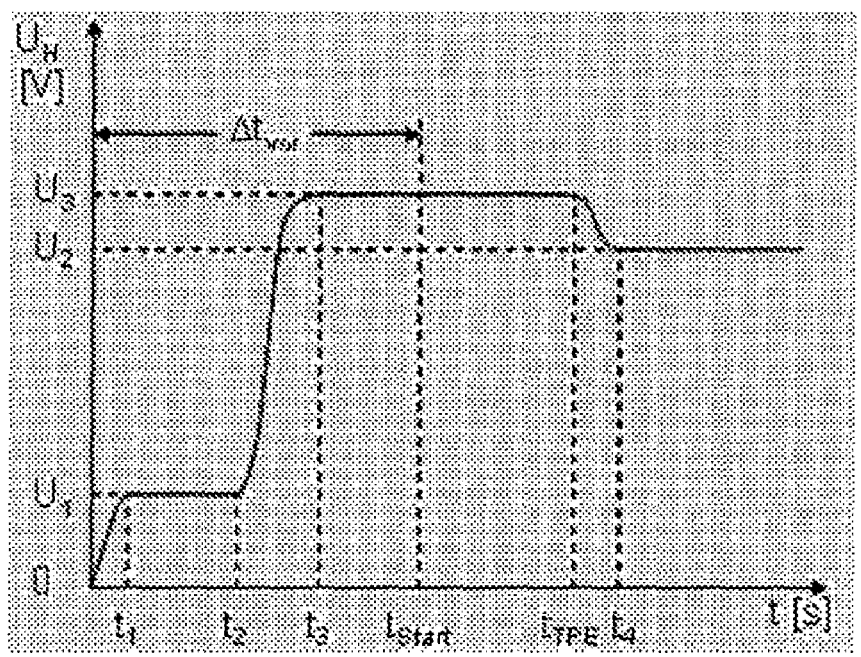
FIG. 3 shows schematically the curve of the voltage present at a heating element during an activation according to the invention.

A possible heating strategy of a lambda probe is depicted in FIG. 2 as well as in FIG. 3, wherein in FIG. 2 the curve of the surface area temperature at the surface area of the sensor is schematically depicted; and in FIG. 3 the corresponding curve of the voltage lying at the heater is depicted.

Provision is made in the operational strategy, which is exemplary presented in FIGS. 2 and 3, for the sensor to be heated up prior to starting the internal combustion engine at a point in time $t_{Start}$. For the purpose of heating the condensate out of the porous layers of the sensor element, where it has collected, the element is heated with a heater voltage $U_1$ to a surface area temperature $T_1=300°$ C. The time taken to heat the condensate out of the porous layers $\Delta t_{aus}=t_2-t_1$ is preferably determined with the quantity of condensate maximally collected $m_{K,max}$, the heat output $P_{H,aus}$, which is applied, and the evaporation enthalpy of the water $\Delta hv$. The following equation is then valid.

$$\Delta t_{aus} = \frac{m_{k,max}}{P_{H,aus}} \cdot \Delta h_V$$

After the condensate has been heated out of porous layers of the sensor element, the surface area of the sensor is heated with the voltage $U_3$ to the shock resistance temperature $T_3$. To heat up the protective pipe, which directly encloses the sensor element, the time duration $\Delta t_{H,SR}=t_{Start}-t_3$ is used for heating. As a result, the entire pre-heating time consists of the time taken to heat the condensate out of the porous layers of the sensor element $\Delta t_{aus}$ and the heating time of the protective pipe $\Delta t_{H,SR}$ with the respective heating ramp times $t_1$ and $t_3-t_2$.

The maximum temperature is maintained up to the achievement of the dew point end TPE at the point in time $t_{TpE}$. Thereafter the sensor surface area is dropped to the standard operational temperature $T_2$ with the voltage $U_2$.

In principle, other temperature curves are also conceivable here. The heating of the condensate out of the porous elements of the sensor element can if necessary be omitted with a suitable sensor, and the sensor can be heated directly to the shock resistance temperature $T_3$ without a heating-up phase.

The invention allows for an immediate readiness for closed-loop control of the lambda probe during engine start-up—0 s operational readiness—, as well as for the operation of the probe at the point of installation—for example downstream from the catalytic converter or as a retracted probe—at which depending upon the application, water impact, respectively thermal shock, is to be expected. This is implemented by an operational strategy, which brings the surface area of the sensor element to a temperature—the shock resistance temperature—, at which potentially impacting drops are reflected due to the film evaporation, which comes into play. This procedural approach can be transferred to all lambda probes. Operating strategies up until now do not allow for a closed-loop control of the exhaust gas emissions prior to the dew point end when cold starting the engine.

The adjustment of the film boiling range on the surface area of the sensor element leads to a spontaneous development of a vapor film between an approaching drop of liquid and the surface area. The drop does not contact the surface area but is reflected, and only a slight heat flow is thus transferred. This effect is known as the Leidenfrost Effect or also as the "Dancing Drop on the Stove Hotplate".

If the protective pipe surrounding the sensor is likewise heated up into the film boiling range, the drop is then likewise reflected there and it moves quickly back and forth between the sensor element and the protective pipe until it is completely evaporated or is carried by the gas stream out of the protective pipe. If the protective pipe is not hot enough and therefore in the range of nucleate boiling, the drop then spreads out completely on the protective pipe surface area and evaporates.

The quick back and forth movement of the water drop is purposely targeted in order to keep the emerging vapor quantity in the protective pipe to a minimum; because in the case of water, an increase in volume of one value greater than 1500 takes place during the phase transition from liquid to vapor. The emerging vapor in the case of nucleate boiling therefore displaces the exhaust gas in the protective pipe, and the possibility arises that the probe does not deliver a signal for the exhaust gas composition.

The temperature, which is referred to in the following as the Leidenfrost temperature, from which a Leidenfrost Effect occurs, is among other things material dependant and can be specifically determined for a given sensor. As a characteristic criterion for identifying from which temperature a Leidenfrost Effect occurs, the evaporation time can be used, which a drop of liquid requires in order to evaporate on a surface area.

Figure 4:
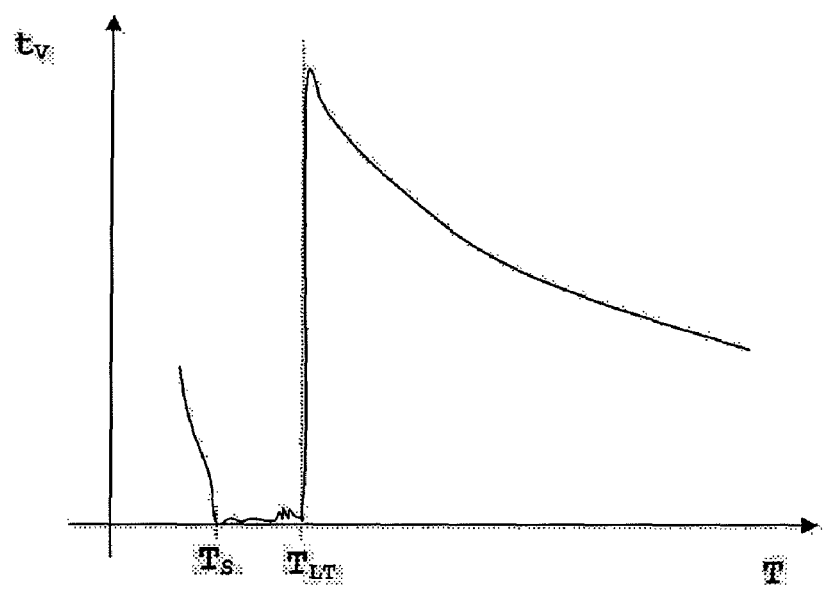
FIG. 4 shows schematically the curve of the time of evaporation as a function of the surface area temperature.

In FIG. 4 such a behavior is schematically depicted. The evaporation time $t_v$ is depicted on the ordinate and the surface area temperature $T_o$ is depicted on the abscissa. The drop of liquid evaporates very quickly in the range of the boiling temperature $T_S$ because the liquid essentially wets the surface area completely, and in so doing a good heat transition is guaranteed from the solid state surface area to the drop of liquid. When the temperature rises, the drop of liquid becomes so hot that a cushion of vapor forms between the drop and the surface area and thermally insulates the drop from the surface area. This insulation effect of the cushion of vapor reveals itself through a marked increase in the evaporation time $t_v$. This increase characterizes in a significant way the so-called Leidenfrost temperature $T_{LT}$.

As previously depicted, a thermal shock of the sensor as a result of water impact is avoided according to the invention, if the surface area temperature of the sensor lies so far above the Leidenfrost temperature $T_{LT}$ that the formation time for the insulating cushion of vapor is shorter than the time for the initiation of checking. In the case of a sensor based on zircon oxide, this effect takes place, for example, at a sensor temperature, respectively surface area temperature, which is higher than 750° C. Water drops, which contact such a surface area, immediately form a cushion of vapor. By way of this insulation and by way of the back and forth movement of the water drops suspended on the cushion of vapor, a regional cooling-down and thereby thermally induced, mechanical tensions in the material are avoided. In so doing, a destruction of or checking formations in the sensor are effectively prevented.

The Leidenfrost temperature depends however not only on the material of the surface area but also on the liquid and its composition, which impacts said surface area. The Leidenfrost temperature for pure water on a zircon oxide surface lies at 470° C., while for the same sensor material this temperature increases, for example, to the previously mentioned 750° C. for the contaminated water drops in the exhaust gas tract.

For temperatures below the Leidenfrost temperature the sensor, respectively the ceramic depending on the material and its durability, fails with varied breakdown probabilities. From this a ceramic material can be derived, whose breakdown probability does not exceed a defined value under all circumstances.

Figure 5:
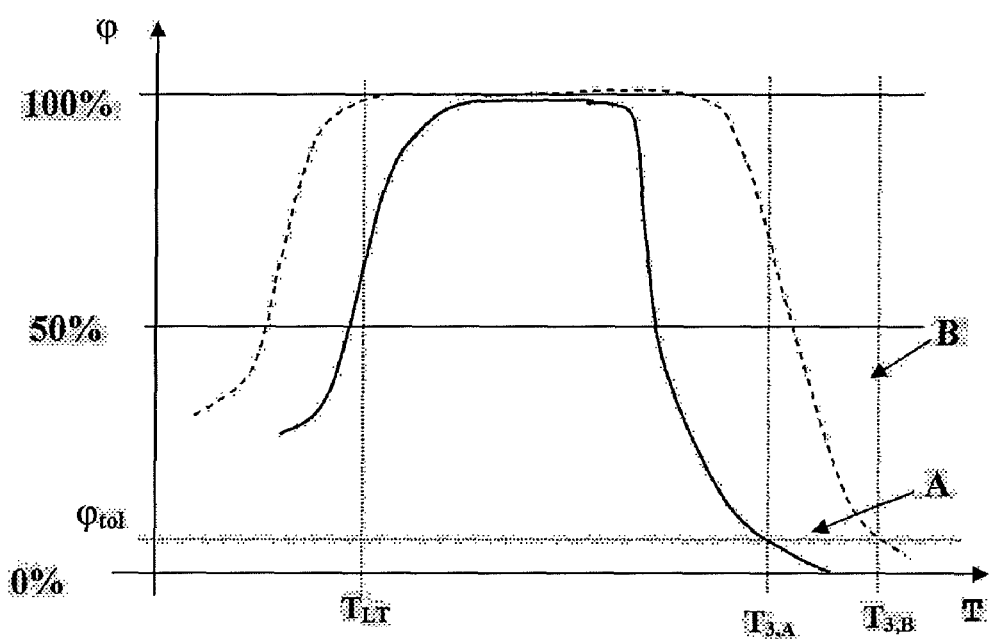
FIG. 5 shows schematically the curve of breakdown probability for ceramics for materials as a function of temperature.

In FIG. 5, a breakdown probability $\phi$ for ceramics from a material A (solid-line curve) and a material B (dashed-line curve) is depicted versus the temperature.

The diagram in FIG. 5 shows that in a known way the breakdown possibility increases as a result of a thermal shock with rising temperature. The breakdown possibility also increases above the Leidenfrost temperature $T_{LT}$ for certain materials—in this instance, for example, material A—up until 100%. Surprisingly, however, the diagram shows that when the temperature additionally increases, the breakdown probability drops again. For a specific sensor material A, B, a corresponding shock resistance temperature $T_{3,A}$, $T_{3,B}$ can be established, at which the breakdown probability $\phi$ remains below a suitable threshold value $\phi_{tol}$. Depending on the application and the wear on the sensor, breakdown probabilities are tolerable, for example, from 100 to 1000 ppm.

By means of a suitable selection or design of the sensor material—for example by alteration of the roughness of the surface area, the size of the pores, the composition of the substrate, etc.—the shock resistance temperature $T_3$ can be influenced.

The invention claimed is:

1. A method of operating a sensor, the method comprising:
   establishing a shock resistance temperature as a function of a breakdown probability of the sensor;
   heating the sensor at least to the shock resistance temperature, wherein the shock resistance temperature is higher than a specific operational temperature; and
   the breakdown probability of the sensor is less at the shock resistance temperature than at the specific operational temperature.

2. A method according to claim 1, further comprising starting a measuring operation of the sensor as soon as the sensor displays the shock resistance temperature.

3. A method according to claim 1, further comprising operating the sensor at a second operational temperature after the sensor has been heated to the shock resistance temperature.

4. A method according claim 3, wherein the second operational temperature is the specific operational temperature.

5. A method according claim 1, further comprising heating the sensor to a first temperature prior to being heated to the shock resistance temperature, wherein the first temperature is lower than the specific operational temperature.

6. A method according claim 1, further comprising heating the sensor to the shock resistance temperature prior to a start-up of an internal combustion engine.

7. A method according to claim 1, further comprising maintaining the shock resistance temperature at least up until a dew point end is achieved.

8. A method according to claim 1, further comprising establishing the shock resistance temperature in such a way that the breakdown probability remains below a tolerable threshold value.

9. A method according to claim 1, wherein the shock resistance temperature is at least as high as a Leidenfrost temperature, wherein at the Leidenfrost temperature water on a surface area of the sensor is subject to a Leidenfrost Effect.

10. A device for operating a sensor, comprising:
a temperature default medium configured to influence a heating of the sensor;
wherein the temperature default medium is configured to establish a shock resistance temperature as a function of a breakdown probability of the sensor; wherein the breakdown probability of the sensor is less at the shock resistance temperature than at a specific operational temperature; and
to operate the heating of the sensor in such a way that the sensor displays at least the shock resistance temperature that is higher than the specific operational temperature.

* * * * *